United States Patent
Orfino et al.

(10) Patent No.: US 6,674,076 B1
(45) Date of Patent: Jan. 6, 2004

(54) HUMIDIFIED IMAGING WITH AN ENVIRONMENTAL SCANNING ELECTRON MICROSCOPE

(75) Inventors: Francesco P. Orfino, Port Moody (CA); Joerg Zimmermann, Vancouver (CA); Lynn C. Erickson, Vancouver (CA)

(73) Assignee: Ballard Power Systems Inc., Burnaby (CA)

( * ) Notice: Subject to any disclaimer, the term of this patent is extended or adjusted under 35 U.S.C. 154(b) by 0 days.

(21) Appl. No.: 10/319,395

(22) Filed: Dec. 12, 2002

(51) Int. Cl.$^7$ .......................... G01N 23/00; G21K 7/00
(52) U.S. Cl. .................. 250/310; 250/311; 250/306; 250/309
(58) Field of Search .................. 250/306, 309, 250/310, 311, 201.3; 73/105; 436/151

(56) References Cited

U.S. PATENT DOCUMENTS

| | | | |
|---|---|---|---|
| 5,412,211 A | * 5/1995 | Knowles | 250/310 |
| 5,674,752 A | * 10/1997 | Buckley et al. | 436/151 |
| 5,828,064 A | 10/1998 | Knowles | 250/310 |
| 6,025,592 A | 2/2000 | Knowles et al. | 25/310 |
| 6,051,825 A | * 4/2000 | Lindsay et al. | 250/201.3 |
| 6,300,630 B1 | * 10/2001 | Veneklasen | 250/310 |
| 6,490,913 B1 | * 12/2002 | Martin et al. | 73/105 |
| 6,590,210 B1 | * 7/2003 | Essers | 250/310 |

FOREIGN PATENT DOCUMENTS

JP 8-292197 11/1996

OTHER PUBLICATIONS

Cameron, R. et al., "Minimizing Sample Evaporation in the Environmental Scanning Electron Microscope," *J. of Microscopy*, vol. 173, pt. 3, pp. 227–237, Mar. 1994.

Danilatos, G., "Introduction to the ESEM Instrument," *Microscopy Research and Technique*, vol. 25, pp. 354–361, 1993.

Thiel, B. et al., "Imaging Heterophase Molecular Materials in the Environmental SEM," *Mat. Res. Soc. Symp. Proc.*, vol. 589, pp. 211–216, 2001.

Thiel, B. et al., "The Study of Water in Heterogeneous Media Using Environmental Scanning Electron Microscopy," *J. of Molecular Liquids*, vol. 80, pp. 207–230, 1999.

* cited by examiner

*Primary Examiner*—John R. Lee
*Assistant Examiner*—Mary El-Shammaa
(74) *Attorney, Agent, or Firm*—Seed IP Law Group PLLC

(57) ABSTRACT

A method and apparatus are described for imaging wet samples with an Environmental Scanning Electron Microscope (ESEM). In particular, a carrier gas is humidified such that the water vapor in the carrier gas in the sample chamber of the ESEM has a partial pressure equal to the saturated vapor pressure of water. Thus, the sample can be imaged without observing any evaporation or condensation thereon. Both the carrier gas and the water vapor may act as the imaging gas within the ESEM. The apparatus is an imaging gas delivery system for the ESEM wherein the carrier gas may be appropriately humidified.

21 Claims, 2 Drawing Sheets

HUMIDIFIED IMAGING WITH AN ENVIRONMENTAL SCANNING ELECTRON MICROSCOPE

BACKGROUND OF THE INVENTION

1. Field of the Invention

The present invention relates to the field of environmental scanning electron microscopes (ESEM) and more particularly to an apparatus and method of operating an ESEM with a wet sample.

2. Description of the Related Art

In a typical environmental scanning electron microscope (ESEM), an electron beam is emitted by an electron gun and passes through an electron optical column of an objective lens assembly. A series of pressure limiting apertures are placed along the column so as to maintain pressure differentials along the column. The pressure may vary from, for example, $10^{-5}$ Pa at the electron gun up to 6000 Pa in the sample chamber through the use of a system of differential pumping. In the electron column, the electron beam passes through magnetic lenses which are used to focus the beam and direct the electron beam through a final pressure limiting aperture. The electron beam is then directed into the sample chamber wherein the beam impinges upon a sample.

The sample chamber is disposed below the vacuum column assembly and is capable of maintaining the sample enveloped in an imaging gas at a desired pressure. In addition to pressure, the temperature of the sample may also be controlled, typically through the use of a Peltier Device in the sample chamber.

The imaging gas may be altered to suit the sample under study and may be, for example carbon dioxide, nitrogen, air, water vapor or argon. Electron backscattering from the sample surface ionizes molecules of the imaging gas and thereby amplifies the signal to be detected. As water vapor is tolerated in the sample chamber, ESEM makes it possible to image wet samples. However, when imaging with water vapor, water evaporation or condensation on the sample should be considered. In some applications, for example, real time hydration or dehydration studies, condensation or dehydration may be desired and the temperature and pressure of the sample can be altered accordingly. However, for most applications, hydration and dehydration are not desired as it may change the sample and alter the corresponding image particularly when operating at low operating temperatures. When using water vapor as the imaging gas, at any pressure, there is a corresponding temperature which represents the saturated vapor pressure. The saturated vapor pressure of a liquid is the partial pressure of the vapor above its liquid state at equilibrium and is dependent on the type of liquid and its temperature.

This is illustrated in FIG. 1, which shows the general relationship between pressure and temperature for water vapor and the plotted line represents the saturated vapor pressure of water. If the pressure is raised or the temperature is lowered from this equilibrium, condensation would occur on the sample. Conversely, if the pressure is lowered or the temperature raised, evaporation would occur. Depending on the equipment used, it may be difficult and time consuming to adjust the pressure and temperature with the ESEM to obtain the saturated vapor pressure equilibrium. For example, control of either or both of the pressure and temperature may not be fine enough to easily obtain the saturated vapor pressure equilibrium particularly at low temperatures where the saturated vapor pressure of water is low. Accordingly, there remains a need in the art for efficiently imaging wet samples with an ESEM, and more particularly, efficiently imaging frozen samples with an ESEM.

BRIEF SUMMARY OF THE INVENTION

An environmental scanning electron microscope is operated at an operating temperature and pressure within a sample chamber. A method of operating such an ESEM comprises:

a. placing a sample in the sample chamber;

b. humidifying a carrier gas such that the partial pressure of water vapor in the carrier gas corresponds to the vapor pressure of water at the operating temperature and the operating pressure; and c. operating the environmental scanning electron microscope with the humidified carrier gas as the imaging gas.

The carrier gas may be any imaging gas, except for water vapor itself, such as, for example, carbon dioxide, air, nitrogen, argon or any combination thereof. The method may be used at low operating temperatures of the ESEM, such as, for example between 0° C. and −40° C. and even as low as −100° C.

The carrier gas may be humidified by, for example, passing the carrier gas over a water reservoir. The water reservoir may be at a low temperature as low as −10° C., −30° C. or even −100° C. and as high as 10° C., 30° C. or even 100° C.

An imaging gas delivery system for an ESEM having a gas inlet comprises:

A. a carrier gas supply;

B. a gas humidifier coupled to the carrier gas supply;

C. a humidity sensor coupled to the gas humidifier; and

D. a delivery valve adapted to receive the gas inlet of the ESEM. When the system is in operation, a carrier gas circulates from the carrier gas supply, through the gas humidifier and humidity sensor to the gas inlet of the ESEM through the delivery valve. Thus the carrier gas becomes humidified and the humidified carrier gas can act as the imaging gas within the ESEM.

A circulation fan may be located between the gas supply and the gas humidifier to assist with flow of the carrier gas through the gas delivery system. Further, a controller may be connected to the system to control the degree of humidification of the carrier gas in response to the humidity sensor.

In an embodiment, the gas humidifier comprises a temperature regulated water reservoir. In such a gas humidifier, temperature control may be affected by, for example, a Peltier device. In another embodiment, the gas humidifier comprises a water injector such that water is directly added to the carrier gas.

These and other aspects of the invention will be evident upon reference to the attached figures and following detailed description.

BRIEF DESCRIPTION OF THE DRAWINGS

In the above figures, similar references are used in different figures to refer to similar elements.

DETAILED DESCRIPTION OF THE INVENTION

Figure 1:
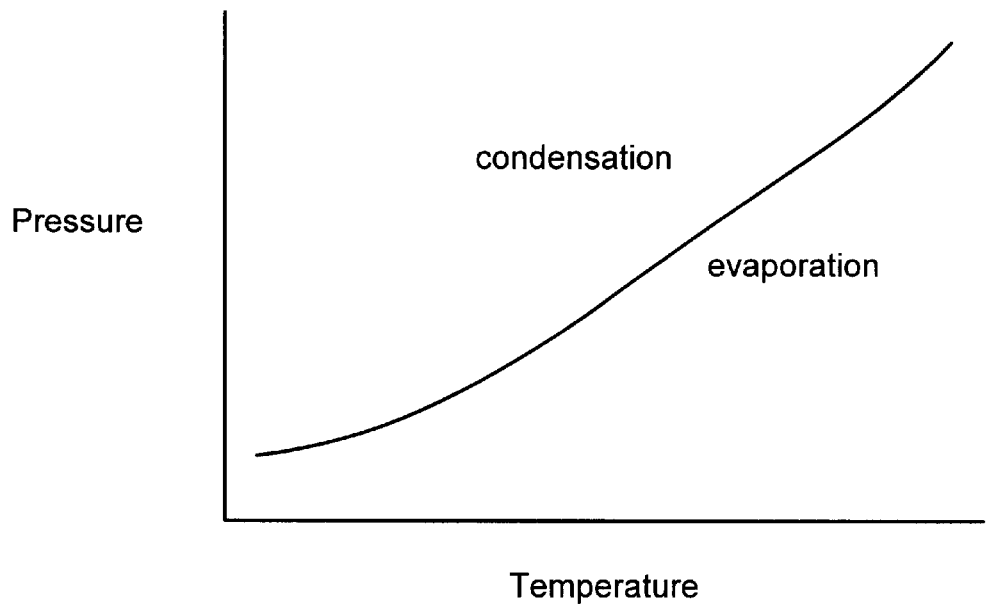
FIG. 1 is a graph illustrating the saturated vapor pressure of water as a function of pressure and temperature.
Figure 2:
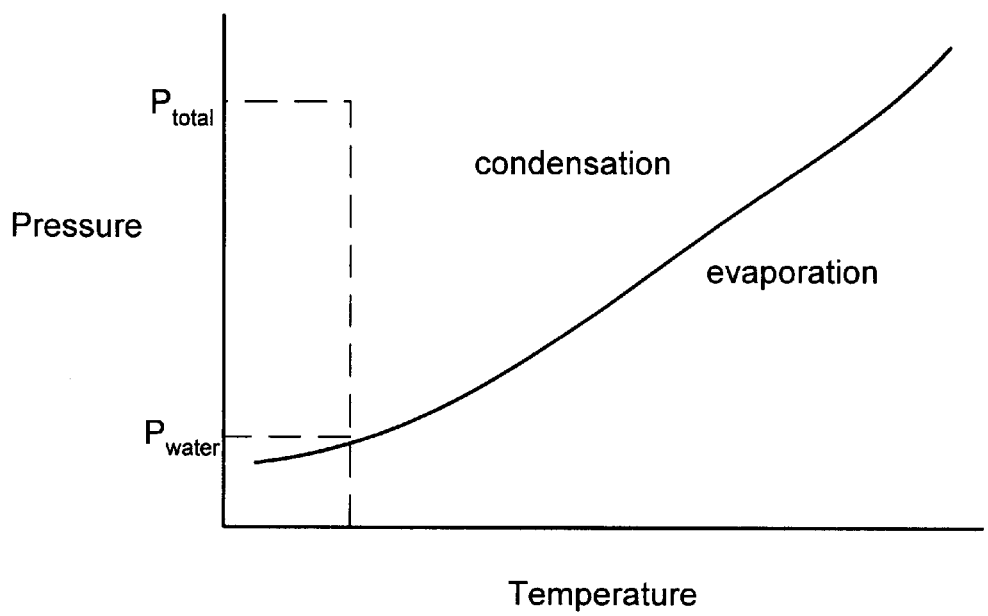
FIG. 2 is a graph illustrating the saturated vapor pressure of water as a function of pressure and temperature with the operating conditions of an ESEM according to the present invention shown.

Dalton's law provides that the pressure exerted by a mixture of gases or vapors enclosed in a given space equals the sum of the partial pressures that each gas or vapor would exert if it alone occupied the same space. The imaging gas used in the environmental scanning electron microscope could be a combination of water vapor and a carrier gas. This is illustrated in FIG. 2 wherein the amount of water vapor present is such as to equal the saturated vapor pressure of water at the operating temperature of the ESEM with an additional carrier gas present to provide the total pressure in the ESEM ($P_{total}$ in FIG. 2). Thus instead of controlling the total pressure or temperature of the sample chamber in the ESEM, the humidity of the carrier gas can be varied to obtain the saturated vapor pressure at the operating temperature. While not limited thereto, this method may be of particular use where the ratio of water vapor to carrier gas is relatively low such as in low temperature operation of the ESEM. Low temperature operation would be, for example, less than 0° C. and as low as −100° C. though more typically, operation would not be less than −40° C. This is illustrated in FIG. 2 where the partial pressure of the carrier gas is greater than the partial pressure of the water vapor.

A further advantage in having a carrier gas at low temperature operation is that better resolution is typically observed from the ESEM since a layer of ice does not form over the sample. Since there may only be a relatively small amount of water vapor needed to arrive at the saturated vapor pressure of water within the sample chamber, the additional carrier gas present may assist with imaging. The carrier gas may be any imaging gas, except for water vapor itself, for example, carbon dioxide, air, nitrogen, argon or any combination thereof.

Figure 3:
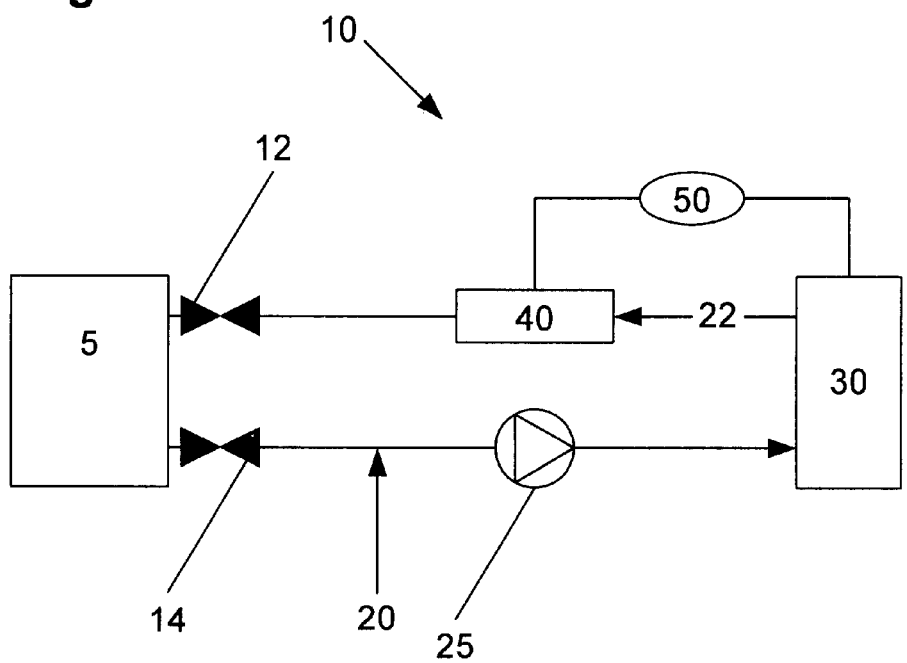
FIG. 3 is a schematic of an imaging gas delivery system for an ESEM.

FIG. 3 illustrates an imaging gas delivery system 10 for an ESEM 5. A carrier gas 20 is injected into system 10. Carrier gas 20 then passes through gas humidifier 30 such that the partial pressure of water vapor in the carrier gas corresponds to the vapor pressure of water in the sample chamber of the ESEM. Humidified carrier gas 22 then passes through humidity sensor 40 to measure the water content therein. A controller 50 may thereby adjust the amount of humidification accordingly of humidified carrier gas 22 in response to the humidity measurement. Humidity sensor 40 may be, for example, an Edgetech Dew Prime I dew point hygrometer.

Circulation fan 25 helps circulate carrier gas 20 through the system and in particular the rate at which carrier gas 20 passes through gas humidifier 30 may affect the degree of humidification. As such, controller 50 may be connected to circulation fan 25 in addition to or instead of being connected to gas humidifier 30. In the embodiment illustrated in FIG. 2, circulation fan 25 is located before gas humidifier 30 though in other embodiments, circulation fan 25 may be located at other points within system 10.

Humidified carrier gas 22 then acts as the imaging gas for the ESEM. Imaging gas delivery system 10 connects to a gas inlet on ESEM 5 through isolation valve 12. The imaging gas may then vent from the sample chamber of ESEM 5 to, for example, the atmosphere. Alternatively, the imaging gas may recycle back into system 10 through isolation valve 14 as shown in FIG. 2.

Figure 4:
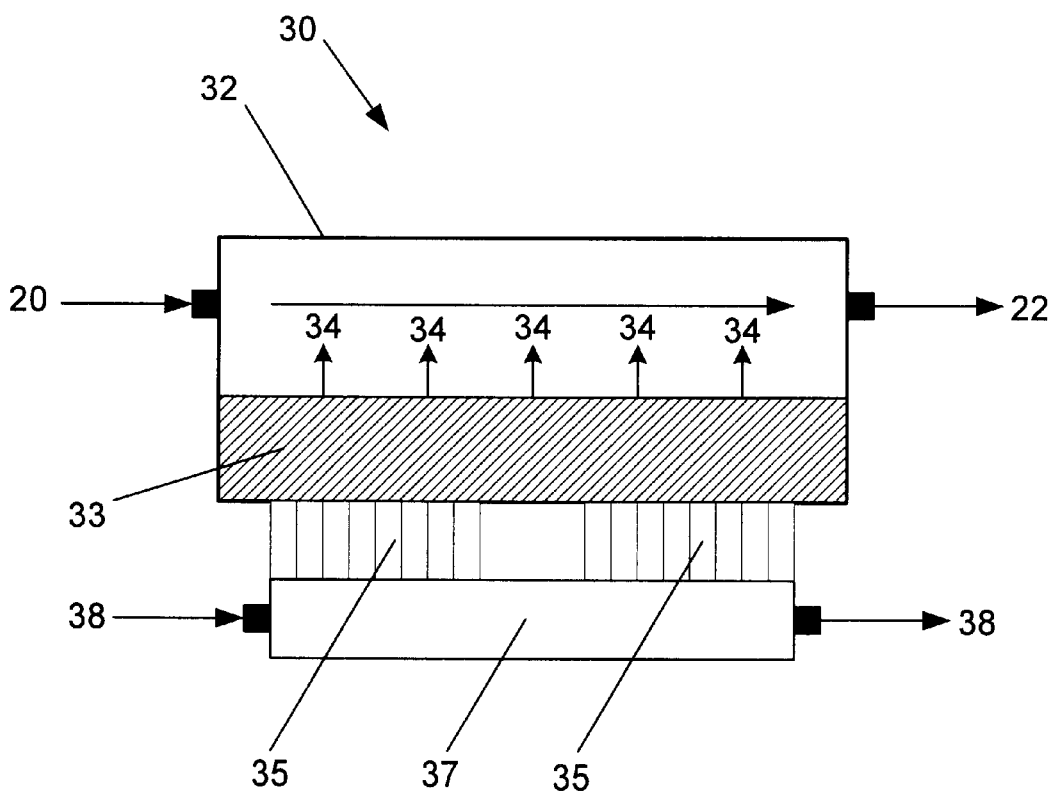
FIG. 4 is a cross-sectional schematic of a gas humidifier.

FIG. 4 illustrates an embodiment of gas humidifier 30 wherein carrier gas 20 passes over water reservoir 33 in humidification chamber 32. The amount of humidification (as depicted by arrows 34) varies depending on the temperature of the water (or ice if the temperature is less than 0° C.) in water reservoir 33, the rate at which carrier gas 20 passes through humidification chamber 32 and the surface area of water within water reservoir 33. In the embodiment illustrated in FIG. 3, the temperature of water reservoir 33 is controlled by a thermoelectric heat exchanger, also known as a Peltier device 35. A coolant 38 flowing through cooling unit 37 acts as a heat sink for the Peltier device 35. Peltier device 35 may cool water reservoir 33 down below 0° C. since ice has a vapor pressure that may be used to humidify carrier gas 20. For most applications, a lower temperature limit for the Peltier device 35 to cool water reservoir 33 would likely be −30° C. However, by reducing the rate carrier gas 20 passes through humidification chamber 32 and/or increasing the surface area of water in water reservoir 33, it may be possible to sufficiently humidify carrier gas 20 for use in ESEM 5 at even lower temperatures. Peltier device 35 may, for example, cool ice reservoir 33 as low as −100° C. Alternatively, Peltier device 35 may heat the water in water reservoir 33 up to 30° C. and perhaps even as high as 100° C. for some applications. Devices such as wicks (not shown) may also be used to increase the effectiveness of the humidification.

In a Peltier device, a number of semiconductor junctions operate at high current density. The semiconductors are chosen to have a relatively poor thermal conductivity so that the heat carried by the electrons which traverse the junctions result in heating of one side of the device with cooling of the other side. Such devices are available from Melcor Corporation of Trenton, N.J. Although the device is composed of alternating bars of p-type and n-type semiconductors, the semiconductors are connected by copper strips so rectifying junctions are not formed. Further, the direction of current flow is easily reversed which results in the heating/cooling to be similarly reversed. For example, if the top plate was cooled initially, reversing the direction of current flow results in heating of the top plate and cooling of the bottom plate. In practice temperature gradients of about 40° C. have been obtained with single stage Peltier Devices operated at one or two amps. Since this may be inadequate for many applications, multistage Peltier devices consisting of two or more Peltier devices stacked one on top of the other may be used. The temperature drops across the Peltier devices are cumulative such that the total temperature drop is obtained by adding together the drop across each device.

In another embodiment of gas humidifier 30 (not shown), water vapor is directly injected into carrier gas 20. A water injector may add controlled amounts of liquid water to a heated element which thereby evaporates the liquid water. The total humidification would vary as a function of the amount of water added as compared to the amount of carrier gas present.

In yet a further embodiment (also not shown), the humidification system may be placed within the interior of the ESEM chamber. In such an embodiment, the hudification system may be part of or separate from the imaging stage within the ESEM chamber.

Although operation of the imaging gas delivery system 10 has been described above with reference to obtaining the saturated vapor pressure of water within the sample chamber at the operating temperature and pressure of ESEM 5, the above system could also be used to obtain condensation or dehydration conditions by varying the degree of humidification of the carrier gas accordingly.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

What is claimed is:

1. A method of operating an environmental scanning electron microscope at an operating temperature and an operating pressure within a sample chamber in the environmental scanning electron microscope, the method comprising:

placing a sample in the sample chamber;

humidifying a carrier gas such that the partial pressure of water vapor in the carrier gas corresponds to the vapor pressure of water at the operating temperature and the operating pressure; and operating the environmental scanning electron microscope with the humidified carrier gas as the imaging gas.

2. The method of claim 1 wherein the carrier gas is carbon dioxide, air, nitrogen, argon or a combination thereof.

3. The method of claim 1 wherein the humidifying a carrier gas comprises passing the carrier gas over a water reservoir.

4. The method of claim 3 wherein the water reservoir is at a temperature between −100° C. and 100° C.

5. The method of claim 3 wherein the water reservoir is at a temperature between −30° C. and 30° C.

6. The method of claim 3 wherein the water reservoir is at a temperature between −10° C. and 10° C.

7. The method of claim 1 wherein the operating temperature is between −100° C. and 0° C.

8. The method of claim 1 wherein the operating temperature is between −40° C. and 0° C.

9. An imaging gas delivery system for an environmental scanning electron microscope having a gas inlet, the system comprising:

a carrier gas supply;

a gas humidifier coupled to the carrier gas supply;

a humidity sensor coupled to the gas humidifier; and a delivery valve adapted to receive the gas inlet of the environmental scanning electron microscope such that when in operation, a carrier gas circulates from the carrier gas supply through the gas humidifier and humidity sensor to the gas inlet of the environmental scanning electron microscope through the delivery valve.

10. The system of claim 9 wherein the carrier gas is carbon dioxide, air, nitrogen, argon or a combination thereof.

11. The system of claim 9 wherein the carrier gas is carbon dioxide.

12. The system of claim 9 further comprising a circulation fan coupled to the gas humidifier.

13. The system of claim 12 wherein the circulation fan is located between the gas supply and the gas humidifier.

14. The system of claim 9 further comprising a controller connected to both the gas humidifier and the humidity sensor.

15. The system of claim 14 further comprising a circulation fan coupled to the gas humidifier and connected to the controller.

16. The system of claim 9 wherein the environmental scanning electron microscope has a gas outlet and wherein the imaging gas delivery system can be coupled to the gas outlet such that when the imaging gas delivery system is in operation, the carrier gas is recycled from the environmental scanning electron microscope back through the imaging gas delivery system.

17. The system of claim 9 wherein the gas humidifier comprises a temperature regulated water reservoir.

18. The system of claim 17 wherein the temperature regulated water reservoir comprises a peltier device.

19. The system of claim 9 wherein the gas humidifier comprises a water injector.

20. An environmental scanning electron microscope comprising the imaging gas delivery system of claim 9.

21. The environmental scanning electron microscope of claim 20 wherein the imaging gas delivery system is within the sample chamber of the environmental scanning electron microscope.

* * * * *